US007538099B1

(12) United States Patent
Hodgen et al.

(10) Patent No.: US 7,538,099 B1
(45) Date of Patent: May 26, 2009

(54) ANTIPROGESTIN METHOD AND KIT FOR REDUCING SIDE EFFECTS ASSOCIATED WITH LOW DOSAGE HRT, ORAL CONTRACEPTION AND REGULATING MENSES

(75) Inventors: Gary D. Hodgen, Norfolk, VA (US); Kristof Chwalisz, Berlin (DE)

(73) Assignee: Eastern Virginia Medical School, Norfolk, VA (US)

( * ) Notice: Subject to any disclaimer, the term of this patent is extended or adjusted under 35 U.S.C. 154(b) by 0 days.

(21) Appl. No.: 08/462,703

(22) Filed: Jun. 5, 1995

Related U.S. Application Data

(63) Continuation of application No. 08/115,008, filed on Sep. 1, 1993, which is a continuation-in-part of application No. 07/843,058, filed on Mar. 2, 1992, now abandoned, and a continuation-in-part of application No. PCT/US93/01931, filed on Mar. 2, 1993.

(51) Int. Cl.
*A61K 31/56* (2006.01)
(52) U.S. Cl. ..................... 514/179; 514/170
(58) Field of Classification Search ................ 514/178, 514/179, 182, 893, 170
See application file for complete search history.

(56) References Cited

U.S. PATENT DOCUMENTS

| 3,890,356 | A |   | 6/1975  | Grunwell et al. | ......... 260/397.5 |
|-----------|---|---|---------|-----------------|---------------------|
| 3,928,398 | A |   | 12/1975 | Grunwell et al. | ......... 260/397.5 |
| 4,018,919 | A | * | 4/1977  | Black           | .......... 424/242  |
| 4,416,822 | A |   | 11/1983 | Campbell        | ........ 260/397.4  |
| 4,670,426 | A |   | 6/1987  | Zor et al.      | ........... 514/171 |
| 4,780,461 | A |   | 10/1988 | Neef et al.     |                     |
| 4,870,069 | A |   | 9/1989  | Ottow et al.    |                     |
| 5,108,995 | A |   | 4/1992  | Casper et al.   |                     |
| 5,116,818 | A |   | 5/1992  | Hodgen et al.   | ............ 514/15 |
| 5,439,913 | A |   | 8/1995  | Chwalisz et al. | ........... 514/277 |
| 5,468,736 | A |   | 11/1995 | Hodgen          | .......... 514/179  |
| 5,516,769 | A |   | 5/1996  | Hodgen          | .......... 514/179  |
| 5,622,943 | A |   | 4/1997  | Hodgen          | .......... 514/179  |

FOREIGN PATENT DOCUMENTS

| EP | 0 129 499 A  | 12/1984 |
|----|--------------|---------|
| EP | 145493       | 6/1985  |
| EP | 0 253 607 A  | 1/1988  |
| EP | 253607       | 1/1988  |
| EP | 639 970 B1   | 3/1995  |
| WO | WO 93/17686  | 9/1993  |
| WO | 93/21926     | 11/1993 |
| WO | 93/21927     | 11/1993 |
| WO | 94/18982     | 9/1994  |
| WO | 94/18983     | 9/1994  |
| WO | 95/17193     | 6/1995  |

OTHER PUBLICATIONS

Ortmann, O., Inhibitory Effects of the Antiprogestin, RU 486, on Progesterone Actions and Luteinizing Hormone Secretion in Pituitary Gonadotrophs, Journal of Steroid Biochemistry, vol. 32, No. 2, pp. 291-297, 1989.*
Chemical Abstracts, vol. 97, 1982. No. 97:156665j.
Chemical Abstracts, vol. 105, 105:897j, (1986).
CA 111(15): 127206n, van Uem et al, 1989.
Conn's Current Therapy, Menopause, Wulf H, Utian, pp. 1017-1020, 1992.
Barbieri et al, A Clinician's Dilemma, HRT and Breast Cancer Risk, Menopause Management, Jul./Aug. 1992, 12-24.
J.F.H.M. van Uem., M.D., Contraceptive Potential of RU 486 by Ovulation Inhibition: I. Pituitary Versus Ovarian Action w/Blockage of Estrogen-Induced Endometrial Prolif., Contraception, Aug. 1989, vol. 40, No. 2, pp. 171-184.
K. A. Steingold, M. D. et al, Antiprogestins in Reproductive Medicine, Sex Steroids, vol. 3, No. 1, Jan. 1992, pp. 233-249.
G. D. Hodgen, PhD., Progesterone Antagonists: Useful for Contraception?, Contemporary OB/GYN Special Issue, pp. 65 and 66, (1988).
Sheth et al, A Randomized, Double-Blind Study of Two Combined and Two Progestogen-Only Oral Contraceptive, Contraception, 25:243, 1982.
Collins et al, Blockage of the Spontaneous Midcycle Gonadotropin Surge in Monkeys by RU 486, J. Clin Endocrinol Metab. 63:1270, 1986.
Danforth et al, Contraceptive Potential of RU 486 By Ovulation Inhibition III Preliminary Observations on Once Weekly Oral Administration, Contraception, 40:195, 1989.
Shoupe et al, Effects of an Antiprogesterone RU 486 in Normal Women II: Administration in the Late Follicular Phase, AM J Obstet Gynecol, 157:1421, 1987.
Liu et al, Disruption of Follicular Maturation and Delay of Ovulation After Administration of the Antiprogesterone RU 486, J Clin Endocrinol Metab, 65:1135, 1987.
Luukkainen et al, Inhibition of Folliculogenesis and Ovulation by the Antigesterone RU 486, Fert Steril, 49:961, 1988.
Batista et al, Delayed Endometrial Maturation Induced by Daily Administration of Antiprogestin RU 486: A Potential New Contraceptive Strategy, AM J Obstet Gynecol, 167:60, 1992.
Messinis et al, The Effect of the Antiprogestin Mifepristone RU-486 On Maturion and In-Vitro Fertilization of Human Oocytes, BR J Obstet Gynecol, 95(6), 1988-Abstract.
Juneja et al, In Vitro Effect of RU 496 On Sperm-Egg Interaction in Mice, AM J Obstet Gynecol, 163:216, 1990.
Chwalisz et al, Inhibition of Estradiol-Mediated Endometrial Gland Formation by the Antigestagen Onapristone in Rabbits: Relationship to Uterine Estrogen Receptors, Endocrinology 129:312, 1991.
Anon, Research Disclosure 28976, 1988.
Hodgen, Surrogate Embryo Transfer Combined With Estrogen-Progesterone Therapy in Monkeys, JAMA 250:2167, 1983.

(Continued)

*Primary Examiner*—Johann R Richter
*Assistant Examiner*—Danielle Sullivan
(74) *Attorney, Agent, or Firm*—Dickstein Shapiro LLP

(57) ABSTRACT

Menses regulation and, when desired, contraception is achieved at low doses of estrogen and progestin, which otherwise would create episodes of breakthrough bleeding and/or withdrawal amenorrhea, by periodically inducing menses with an antiprogestin.

40 Claims, No Drawings

OTHER PUBLICATIONS

Chillik et al, Characterizing Pituitary Response to Gonadotropin-Releasing Hormone (GnRH) An-tagonist in Monkeys: Tonic Follicle-Stimulating Hormone/Luteinizing Hormone Secretion Versus Acute GnRH Challenge Tests Before, During and After Treatment, Fert. Steril, 48:480, 1987.

Yoshimura et al, Progesterone Protects Oocytes From Premature Degeneration Within the Follicle, Nippon Sanka Fujinka Gakkai Zasshi, 42(9):1256, 1990-Abstract.

Sakiz et al, R 2323-An Original Contraceptive Compound, Excerpta Medica, Abs. 86, 1970.

Spitz, Clinical Applications of the Antiprogestin RU 486, The Endocrinologist, 3:58, 1993.

Gravanis et al, Endometrial and Pituitary Responses to the Steroidal Antiprogestin RU 486 in Postmenopausal Women, J. Clin. Endocrinol. Metab. 60:156, 1985.

Wolf et al, Noncompetitive Antiestrogenic Effect of RU 486 in Blocking the Estrogen Stimulated Luteinizing Hormone Surge and the Proliferative Action of Estradiol on Endometrium in Castrate Monkeys, Fert. Steril., 52:1055, 1989.

Kettel et al., "Endocrine responses to long-term administration . . . ", *Fertility and Sterility*, vol. 56 (3), pp. 402-407, Sep. 1991.

Chwalisz et al., "Evaluation of the Anti-Proliferative Actions . . . ", Abstract No. 417, *Soc. for Gynecologic Investigation-Scientific Prog. and Abs.*, 39th Annual Mtg., San Antonio, TX, p. 317, Mar. 18-21, 1992.

Chwalisz et al., "Functional Antioestrogenic Action of Progesterone . . . ", *Current Concepts in Fertility Req. and Repro.*, Ed. Puri et al., pp. 411-428, 1994.

Genevieve Azadian-Boulanger et al., "Hormonal Activity Profiles of Drugs for Endometriosis Therapy," *Medical Management of Endometriosis*, pp. 125-148 (1984).

Marilyn J. Koering et al., "Morphologic response of endometrium to a progesterone receptor antagonist, RU486, in monkeys," *Fertility and Sterility*, vol. 45, No. 2, pp. 280-287 (1986).

J. Neulen et al., "Influence of the antigestagens ZK 98.299 and ZK 98.734 on the production of prostaglandin F2α (PG F2α) and prostaglandin E2 (PG E2) in human endometrium in vitro," *Acta Endocrinologica. Supplementum*, V. 114, pp. 7-8 (1987).

Tetsuro Kawano et al., "Effect of RU 486 on Glycogen Metabolism in Endometrium," *Acta Obstetrica Et Gynaecologica Japonica*, vol. 41, No. 10, pp. 1507-1511 (1989).

Raimo Kekkonen et al. "Interference with ovulation by sequential treatment with the antiprogesterone RU486 and synthetic progestin," *Fertility and Sterility*, vol. 53, No. 4, pp. 747-750 (1990).

Ov D. Slayden et al. "Estrogen Action in the Reproductive Tract of Rhesus Monkeys During Antiprogestin Treatment," *Endocrinology*, vol. 132, No. 4, pp. 1845-1856 (1993).

Irving M. Spitz et al. "Progesterone Antagonists on the Horizon," *Clinical Obstetrics and Gynecology*, vol. 32, No. 2, pp. 403-413 (1989).

Chander P. Puri "Effects of Antiprogestins on Folliculogenesis, Corpus Luteum Function and Endometrium of Primates: Emerging Contraceptive Strategies," *Current Concepts: Fertility Regulation and Production*, pp. 445-462.

Wulf H. Utian "Menopause," *Conn's Current Therapy*, pp. 1017-1020.

Wolf, J.P. et al. (1987), *Biol. Reprod*. 36 (Supp. 1), p. 109.

D. Healy et al., "Induction of Menses by Antiprogesterone Steroid (RU 486) in Primates: Site of Action, Dose-Response Relationships, and Hormonal Effects," Fertility and Sterility, vol. 40, No. 2, 1983, pp. 253-257, XP008002911.

C.F. Chillik et al., "RU486-Induced Menses in Cynomolgus Monkeys: Uniformity of Endometrial Sloughing," Fertility and Sterility, vol. 45, No. 5, May 1986, pp. 708-712, XP001068224.

H.B. Croxatto et al., "Late Luteal Phase Administration of RU486 For Three Successive Cycles Does Not Disrupt Bleeding Patterns or Ovulation," Journal of Clinical Endocrinology and Metabolism, vol. 65, Dec. 1, 1987, pp. 1272-1277, XP008002486.

B. Shortle et al., "Effects Of An Antiprogesterone Agent, RU-486, On the Menstrual Cycle of the Rhesus Monkey," Journal of Clinical Endocrinology and Metabolism, vol. 60, No. 4, Apr. 1985, pp. 731-735, XP001068228.

V.G. Garzo et al., "Effects of An Antiprogesterone (RU486) on the Hypothalamic-Hypophyseal-Ovarian-Endometrial Axis During the Luteal Phase of the Menstrual Cycle," Journal of Endocrinology and Metabolism, vol. 66, No. 3, 1998, pp. 508-517, XP008002478.

L.K. Nieman et al., "Use of Single Doses of the Antiprogesterone Steroid RU 486 for Induction of Menstruation in Normal Women," 1985, Plenum Press, New York & London, XP001076665 in "The Antiprogestin Steroid RU 486 and Human Fertility Control," Baulieu, E.E., Segal S.J. (eds.).

D. Philibert, "RU38486 An Original Multifaceted Antihormone in Vivo," 1984, Walter De Gruyter, Berlin, Germany, XP008002479 in Adrenal Steroid Antagonism Agarwal MK (ed.).

L.K. Nieman et al., "The Progesterone Antagonist RU 486," The New England Journal of Medicine, vol. 316, No. 4, Jan. 22, 1987, pp. 187-191, XP000564124.

D. Shoupe et al., "Effects of the Antiprogesterone RU 486 in Normal Women," American Journal of Obstetrics and Gynecology, vol. 157, Dec. 1987, pp. 1415-1420, XP008002485.

H.P. Zahradnik et al., "Antigestagene-Grundiagen und Klinik," Archives of Gynecology and Obstetrics, vol. 250, No. 1, 191, pp. 861-868, XP008002752.

E. E. Baulieu et al., "Antiprogesterone Activity of RU 486 And Its Contragestive And Other Applications," Human Reproduction, vol. 1, No. 2, 1986, pp. 107-110, XP000564113.

K. Parfitt (Ed.) "Martindale—The Complete Drug Reference, 32rd edition," 1999, Pharmaceutical Press, London, XP002198132.

Chwalisz et al., "Functional Antiestrogenic Action Of Progesterone Antagonists In The Non-Pregnant Uterus," *International Conference on Fertility Regulation, Programme and Abstracts*, Nov. 5-8, 1992, Bombay, India, p. 64.

Schmidt et al., The New England Journal of Medicine, vol. 324, No. 17, pp. 1174-1179 (1991).

* cited by examiner

ANTIPROGESTIN METHOD AND KIT FOR REDUCING SIDE EFFECTS ASSOCIATED WITH LOW DOSAGE HRT, ORAL CONTRACEPTION AND REGULATING MENSES

This is a continuation of the application Ser. No. 08/115,008 filed Sep. 1, 1993, which is a CIP of Ser. No. 07/843,058 of Mar. 2, 1992 now abandoned.

This is a continuation-in-part of application Ser. No. 07/843,058, filed Mar. 2, 1992, and of PCT Application PCTUS93/01931, filed Mar. 2, 1993.

BACKGROUND OF THE INVENTION

This invention relates to a method and kit for regulating menses and/or reducing the side effects, such as unscheduled bleeding, in pre-, para- and post-menopausal females on low dosage estrogen and/or with estrogen-progestin therapy and for achieving oral contraception in gonadal female mammals.

Although inhibition of ovulation in the form of estrogen/progestin combination oral contraceptives has been the most effective strategy for achieving reversible pharmacological fertility control in women, because of the known adverse side-effects associated with long term contraception by this method, especially in women who smoke in the 40-44 age group, over the years interest in achieving contraception at lower estrogen doses has developed.

Thus, during the over 30 year history of combined estrogen/progestin oral contraception, there has been a steady downward adjustment of the daily estrogen dosage, both for oral contraceptive purposes in premenopausal female and for estrogen replacement therapy in post-menopausal females. See, e.g., EP-A-0 253,607, which discloses, as a preferred embodiment, administering to pre-menopausal females daily a tablet containing 1 mg of 17β-estradiol and 0.075 ml of levonorgestrel for 23 or 24 (23-26) days followed by 5 or 4 (2-5) "pill free" or blank-pill days, for a total of 28 days per cycle, and the references cited therein, the disclosures of all of which are incorporated herein by reference.

Concurrently, although the progestin component has been lowered somewhat also, reduced androgenicity has remained an ongoing priority. Together, these adaptations of formulation have been presented in a variety of regimens, both monophasic and multiphasic. As a result, today's oral contraceptives are much safer with regard to the incidence and severity of estrogen-linked clotting disorders, as well as the cumulative impact of more "lipid friendly" progestins that maintain high density lipoprotein cholesterol levels in circulation. See, Spellacy, W N et al.,; "Am J Obstet Gynecol" 1980; 137; 109; Scott, J Z et al., "Fertil Steril" 1978; 30:141; Mishell, D R Jr. et al., "J Reprod Med." 1990; 35 (Suppl. 4): 447-481; Speroff L., "Contemp Obstet Gynecol" 1991; 36:65; Meilis G B et al., "Contraception" 1991; 43; 23; and Stamplfer M J, Willett W C et al., "Am J. Obstet Gynecol" 1990; 163: 285.

This evolution of oral contraceptive formulations advanced most rapidly in Europe and has been steadily emerging in America as well. Indeed, the accumulating data based on oral contraceptive pills containing only 20 to 35 µg of estrogen per day spurred the Food and Drug Administration's Fertility and Maternal Health Drugs Advisory Committee to indicate low dose oral contraceptives for healthy, non-smoking women during the perimenopausal years (such as ages 35 to 50) [See Mishell (1990) and Speroff (1991)], supra; U.S. Food and Drug Administration, Advisory Committee on Maternal and Reproductive Health, 1989, Rockville, Md.; and Rosenberg, L. et al. JAMA 1985; 253:2965. In Japan, oral contraceptives are now being evaluated for safety and efficacy criteria for the first time, with anticipation of general availability to physicians and patients within about one year.

In addition to maintenance of contraception efficacy when the female is gonadal a principal issue involved when considering lowering the daily dose of estrogen-progestin medications in oral contraceptives even lower, is avoidance of further erosion in the control of endometrial bleeding. Whereas even the lowest dose oral contraceptive products available now have demonstrated sustained contraception efficacy, overall the incidence of bleeding control problems, which manifest themselves both in breakthrough bleeding (untimely flow or spotting) or withdrawal amenorrhea during the "pill free" week (expected menses), has increased as estrogen/progestin doses are reduced. See Gray, R H. in "Endometrial Bleeding and Steroidal Contraception"; Diczfalusy E, Fraser R S, Webb FTE (Eds). Bathe, England: Pittman Press; 1990: 14-19, and Cullbey G. et al., "Contraception" 1982; 26:229. The same problem is associated with low dosage hormonal replacement therapy (HRT).

OBJECTS OF THE INVENTION

It is an object of this invention to solve the bleeding control problem associated with low dosage estrogen, and/or of progestin hormone replacement therapy (HRT).

It is another object of this invention to provide a method for achieving contraception in a gonadal female mammal at ultra low estrogen and/or progestin oral doses without the breakthrough bleeding and/or amenorrhea which is associated therewith.

Another object is to provide such a method which permits a normal menses and which regulates the onset thereof.

Still another object is to provide such methods in which the medication is self-administered.

A further object is to provide such methods which do not have the side effects associated with conventional or low oral dosage estrogen-progestin oral contraception or hormonal replacement therapy.

Another object is to provide kits for practicing the methods of this invention.

Another object is to provide a pharmaceutical composition effective to induce menses in a female on estrogen/progestin oral contraception or estrogen and/or progestin hormonal replacement therapy (HRT).

Other objects will be apparent to those skilled in the art to which this invention pertains.

SUMMARY OF THE INVENTION

In a method aspect, this invention relates to a method of avoiding the bleeding problems associated with administering to a female mammal dosage amounts of an estrogen, alone or in combination with a progestin, low enough to create incidents of breakthrough bleeding and withdrawal amenorrhea, which comprises periodically inducing menses by administering to the female an amount of an anti-progestin effective to induce sloughing of accumulated endometrial tissue.

In one article of manufacture aspect, this invention relates a pharmaceutical composition adapted for oral ingestion comprising a unit dosage containing a menses inducing dosage amount of an antiprogestin, arranged to be ingested after ingestion for at least 20, e.g., 20-180, consecutive days of at least 20, e.g., 20-180, unit dosages containing amounts of an estrogen and/or progestin effective to provide HRT in para- or post-menopausal female but which are too low bleeding and/or withdrawal amenorrhea. In another article of manufacture aspect, the amounts of the estrogen or estrogen and progestin are effective to achieve oral contraception in a gonadal female when such amounts have been ingested daily without interruption for a least 20 days by a gonadal female.

In another article of manufacture aspect, this invention relates to a kit containing and arranged in a conventional manner, e.g., like Berlex Laboratories "Levien 21", at least 20 oral dosage units, each containing an estrogen and optionally a progestin in some or all of them, in amounts which collectively are effective, when one dosage unit thereof is ingested daily for 20 or more days, to achieve either HRT in a para- or post-menopausal female human being or oral contraception in a gonadal female human being, but which promote incidents of breakthrough bleeding and/or withdrawal amenorrhea.

In a first embodiment of the kit aspect of this invention, an additional oral dosage unit, containing only a menses-inducing amount of an antiprogestin, is positioned so as to be ingested after ingestion of the 20 or more estrogen/progestin oral dosage units. In one variation of this embodiment of the kit, the number of estrogen/progestin-combination oral dosage units which precedes the antiprogestin-containing oral dosage units is increased, e.g., to 21 or more, e.g., 21 or up to 180 units. In another variation, intended for use on estrogen replacement therapy by para- and post-menopausal females, the progestin is omitted from some or all of the tablets. These variations are for individuals who wish to extend the length of their medically regulated menstrual cycles beyond the usual 4 week term.

In a second embodiment of the kit aspect of this invention, positioned to be taken after the 20 or more oral dosage units of the first embodiment described above, e.g., like Berlex Laboratories "Levien 28", are 6 or more placebo oral dosage units to maintain a "one-pill-a-day" regimen and remind the individual when to begin a new cycle of administration.

In a third and preferred embodiment of the kit, instead of the 6 or more placebo oral dosage units described above, the kit contains 28 or 29 or 30 oral dosage units, each of which contains a low dosage amounts of estrogen and progestin corresponding to the first 21 dosage units of the first embodiment. In this embodiment, the dosage unit arranged to be taken on the 22nd day also contains a menses inducing amount of the antiprogestin.

DETAILED DESCRIPTION

This invention is based on the discovery that incidents of breakthrough bleeding and withdrawal amenorrhea the frequency of which increase when oral contraception is achieved employing lower than conventional estrogen and progestin dosages can be minimized or avoided completely by inducing menses with an anti-progestin, either during the "drug-free", i.e., estrogen- and progestin-free, week of the monthly cycle of daily for about 21 days estrogen and progestin oral administration or preferably whenever a menses is desired during uninterrupted daily estrogen or estrogen and progestin administration.

Also, a normal menses can be achieved with an anti-progestin without interrupting a concurrent continuous low dose estrogen/progestin oral contraceptive regimen. A continuous ultra low dose estrogen/progestin oral contraception regimen in combination with periodic, e.g., at 30, 60 or 90 days intervals, administration of an antiprogestin, e.g., RU 486, provides predictable menstrual control.

The physiological rationale for this approach is to maintain a lesser degree of pharmacologic inhibition of the pituitary-ovarian-uterine axis, but by an uninterrupted regimen to avoid "follicular escape". With today's lower dose oral contraceptive products, robust ovarian follicular growth can resume more quickly during the "pill free" interval than when higher dose pills were used in former decades. In turn, enhanced endogenous estradiol secretion with rapid endometrial proliferation, all known to accelerate during the "pill-free" 7-day period, results in less intermenstrual breakthrough bleeding, and less withdrawn amenorrhea as well. The intermittent administration of the progesterone antagonist is scheduled so as to ensure sloughing of the accumulated endometrial tissue at every fourth week or at extended intervals, e.g., every 60, 90, 120, 150, 180 or more days, without pill-free interruption of the oral contraceptive regimen.

The intermittent, i.e., about monthly or longer, e.g., di- or tri-monthly, quarterly or semi-annually, administration of an anti-progestin to induce menses according to this invention avoids abnormal bleeding problems, e.g., breakthrough bleeding and withdrawal amenorrhea, by maintaining follicular phase level of endogenous serum estradiol at a higher level than that associated with conventional low dosage estrogen/progestin oral contraception.

In the normal menstrual cycle, progesterone is produced from the corpus luteum created after ovulation. In the contraceptive method of this invention, a progestin is administered along with an estrogen, at least toward the end of each regulated cycle, e.g., during about the last two weeks of each cycle, in order to convert proliferative endometrium to the secretory phase, thereby reducing the risks of endometrial carcinomas associated with unopposed estrogen action. However, menses is achieved with the anti-progestin alone, irrespective of whether or not administration of the estrogen and/or the progestin is interrupted during the menses week of the menstrual cycle when the anti-progestin is administered.

The daily oral doses of estrogen and progestin which are administered generally are the lowest which will achieve reliable contraception or hormone replacement therapy in women, viz., doses contraceptively equivalent to about 5 to 35 mcg. of ethinyl estradiol and about 0.5 to 1.5 mg. of norethindrone acetate. The daily doses can be the same throughout the month or can vary from week to week, as in the case of Berlex Laboratories "Tri-Levien", e.g., when a monthly menses is desired, in which case the doses of both or either can be lowered or eliminated during the menses week of the cycle. However, if administration thereof is eliminated or lowered during the menses week, the dosages thereof during the other weeks of the cycle preferably are increased accordingly, e.g., during the second and especially during the third weeks to ensure that breakthrough bleeding does not occur prior to menses.

Similarly, when a monthly menses is not desired, e.g., in the case of post-menopausal females, the dosage of the estrogen and/or the progestin can periodically be briefly increased, e.g., at a predetermined period after the last menses, above the base-line long term dosage, to suppress isolated instances of breakthrough bleeding as a result of low levels of estrogen and/or progestin administration over a protracted period of time.

Examples of progestins which can be employed in this invention are micronized progesterone (15-50 mg/day), norethindrone and esters, e.g., acetate, thereof (0.1-0.75 mg/day), norethynodrel (0.3-0.6 mg/day); ethynodiol diacetate (0.3-0.75 mg/day), norgestrel (0.75-0.2 mg) and levo-norgestrel (0.03-0.1 mg/day), chlormadinone acetate, cyproterone, acetate, norethindrone, desogestrel, norgestimate, dihydrospirenone, levo-norgestrel, and gestodene (Schering A G, Berlin; U.S. Pat. No. 4,081,537) (equivalent to 0.03-0.15 mg levo-norgestrel.

For a listing of compounds see the articles from the book by B. Runnebaum et al., "Female Contraception: Update and Trends", Springer-Verlag, Berlin, 1988, pp. 64-190, 109-121, 122-128, and 129-140; which disclose progestationally active compounds. See for example, page 65 and pages 68-70 which list various progestins; pages 110 and 111 (FIG. 1 and Table 1) which list synthetic progestagens; page 122, FIG. 1 which list gestagens; and pages 129-133 (FIGS. 1-10) and page 137, Table 2 which list progestagens, or the long acting esters of estriol, described in U.S. Pat. Nos. 4,681,875 and 4,738,957.

Examples of estrogens which can be employed in this invention are ethinyl estradiol and estradiol and their esters, e.g., acetate, valerate, benzoate and undecylate, (5-15 mcg/day) mestranol (20-25 mcg/day), and conjugated estrogens (5-15 mcg/day).

The progestin and estrogen can be administered in the conventional manner by any route that the selected progestin and estrogen is active, e.g., orally, by intramuscular injection, transdermally or by way of a vaginal ring. Most estrogens and the synthetic progestins are orally active and therefore are preferably administered by that route, e.g., in the form of a tablet, dragee, capsule or pill. If the progestin and/or estrogen is to be administered in tablet or dragee form, the latter, may optionally contain a pharmaceutically acceptable carrier, e.g., a binder, such as tragacanth, corn starch or gelatin; a disintegrating agent, such as alginic acid; and a lubricant, such as magnesium stearate. Also, the estrogen and/or progestin may be delivered transdermally.

The estrogen and/or progestin preferably is administered without interruption, since the anti-progestin alone is effective in inducing menses, or administration thereof can be interrupted during or prior to menses, e.g., beginning on day 1 of anti-progestin administration and for up to about 6 days thereafter. Thus, the estrogen and progestin can be administered uninterrupted at lower than conventional doses for up to 6 months or longer, during which time, menses can be induced at a desired and preselected frequency, e.g., every 20, 30, 60, 90, 120, 150 or 180 days, by administrating a menses-inducing amount of the anti-progestin 1, 2 and/or 3 days prior to the desired day of onset of menses.

Examples of anti-progestins which can be employed in this invention are RU 486 ("Mifepristone", Roussel Uclaf, Paris); and "Onapristone" (Schering Ag, Berlin; U.S. Pat. No. 4,780, 461) and the steroids described in the following patents and patent applications: U.S. Pat. No. 4,609,651, especially the compound lilopristone (11β-(4-dimethylamino-phenyl-17β-hydroxy-17α-(3-hydroxy-prop-1-(Z)-enyl-4,9(10) estradien-3-one); U.S. application Ser. No. 06/827,050, especially the compounds 11β-4-acetylphenyl)-17β-hydroxy-17α-(1-propinyl)-4,9-estradien-3-one and 11β-(4-acetylphenyl)-17β-hydroxy-17α-(3-hydroxy-1(2)-propenyl)-4,9-estradien-3-one; U.S. application Ser. No. 07/283,632; U.S. application Ser. No. 07/541,806, corresponding to published European patent application EP-A 04042831; and other anti-gestagens, e.g., U.S. Pat. No. 4,891,368. The amount of the anti-progestin administered, in a single or in divided doses over a 24-72 hour period typically is about 50 to 500 mg. The minimum amount required to predictably induce menses can readily be determined by routine clinical experiments.

After the antiprogestin is administered, e.g., in a single dose or in divided doses on the same day or on successive days, menses is usually achieved within about 3-4 days thereafter.

Optionally, the antiprogestin can be administered in admixture with a daily dose of the estrogen and progestin on an appropriate day or days of the cycle, e.g., day 20 or any day thereafter, e.g., day 30, 60, 90, 120, 150 and/or 180.

In its article of manufacture embodiment, this invention relates to materials, reagents and kits for practicing the methods of this invention.

In its kit aspect, this invention is directed to an otherwise conventional multiple dosage unit article of manufacture comprising 20 or 28 dosage units adapted for oral-administration. All versions contain in their first 20 or more units collectively, an amount of an estrogen and a progestin effective, when one dosage unit thereof is self-administered on 21 successive days, to block folliculogenesis for one cycle but which is less than the amount thereof effective to avoid incidents of bleeding problems. The last dosage unit of the 21 dosage units version and the 22nd dosage unit of 22 and 28 dosage units versions contain an amount of an antiprogestin effective to prevent incidents of bleeding problems and induce menses. The 22nd to 28th dosage units of the 28 dosage units version either contain, like the first 21 dosage units, low dosage amounts of estrogen and progestin.

Preferably, the dosage units containing the estrogen and progestin and/or antiprogestin are adapted for oral administration but can alternatively be adapted for sublingual, rectal, vaginal or topical (on the skin) application. Preferably also, units adapted for oral ingestion are in the form of tablets, capsules or dragees. Preferably further, the antiprogestin is contained in the same unit or units containing the estrogen and the progestin.

The pharmaceutical compositions employed in the process of this invention will usually contain the anti-progestin in conjunction with a conventional, pharmaceutically acceptably carrier. Usually, the effective dosage of the anti-progestin is from about 1.0 to about 10 milligrams per kilogram of the body weight of the host when given orally. Effective dosages will vary with the selected mode of administration and the particular species of mammal being treated.

In a pharmaceutical composition aspect, this invention relates to an oral dosage form, e.g., pill, tablet, caplet or capsule or liquid, containing a menses-inducing amount of the antiprogestin, in admixture with the amount which is orally contraceptive, when corresponding amounts thereof are ingested by a gonadal female mammal on 21 successive days, of an orally active estrogen or an orally active progestin and, optionally, a conventional pharmaceutically acceptable carrier, e.g., binder, filler or diluent in the case of a solid dosage form, or an aqueous or alcoholic liquid, e.g., as described herein above. The composition is intended to be ingested by an individual on a continuous or sequential estrogen and progestin contraceptive regimen e.g., conventional combined daily oral estrogen and progestin ingestion, when a menses is desired.

The pharmaceutical composition of this invention permits dispensing the oral estrogen/progestin in bulk forms, e.g., in bottles of 30, 60 or 100 tablets or capsules or in bottles of liquid, since the daily dosage thereof can remain unchanged throughout the period of administration.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, cited above and below, are hereby incorporated by reference.

EXAMPLES

Example I

Intermittent antiprogestin administration During Continuous Ultra Low Dose Contraception Primates Thirty-four adult female rhesus monkeys (*Macaca mulatta*) having regular presumptively ovulatory menstrual cycles (28.7±3.4 days for the month prior to study entry) were selected. Their duration of spontaneous menses was 3.7±1.6 days. These primates are worthy laboratory surrogates for investigations pertinent to human oral contraceptive use because of extensive physiologic similarities to the functions of the hypothalamic-pituitary-ovarian-uterine axis in women. See Hodgen, G D., "Fertil Steril 1982; 38:281; Danforth D R. et al., "Contraception" 1989; 39:321; and van Uem JFHM, et al., "Contraception" 1989; 40:171.

Mean body weight of the monkeys was 5.8±1.6 kg (X±SEM). They were housed individually in a controlled environment (12 hours of light and 23° C.). Their diet was a commercial primate food (Purina, St. Louis, Mo.) with water ad libitum.

The Eastern Virginia Medical School maintains a fully accredited animal research facility which complies through its Animal Care and Use Committee with the review standards set forth in the National Institutes of Health's "Guide for Care and Use of Laboratory Animals", the Public Health Services' "Principles for the Care and Use of Laboratory Animals", and the United States Department of Agriculture's Implementation Regulations of the 1985 amendments for the Animal Welfare Act.

Study Design

The study was conducted in two parts: Part I was an adaptation interval of three oral contraceptive treatment cycles, each of which consisted of oral medication by gavage for 21 days followed by 7 no treatment days, thus mimicking the traditional regimen of commercial oral contraceptive pill packages. This design assured that all (32 monkeys completed the course) individuals would be exposed during the initial adjustment interval, to a medication regimen for which prior human data has shown a transiently higher incidence of breakthrough bleeding than occurs among longer-term contraceptive users. See Gray (1990); Culbey et al. (1982), supra. Vaginal swabs (cotton tipped applicators moistened in 0.9% saline) and other hands-on procedures were performed daily between 7 and 9 a.m. to detect bleeding (recorded subjectively as spotting, moderate flow or overt menses). In treatment cycle 2 only, but including the antecedent week, daily blood samples were collected from a femoral vein under light ketamine anesthesia (30 to 50 mg, in Vetalar, Parke Davis, Morris Plains, N.J.). Serum was harvested and frozen (−15° C.) until radioimmunoassay of estradiol and progesterone (Danforth et al. (1989); van Vem et al., (1989) supra, which was completed before starting Part II of the study, thereby insuring that ovulation inhibition was achieved by the ultra low dose regimens.

In Part II, 30 of these primates were randomly assigned to five treatment groups of six each: (1) the oral contraceptive medication employed in Part I was continued (21+7 day regimen) for 6 months; (2) continuous (no "pill-free" interval) daily estrogen-progestin medication, with combined single day oral administration of an antiprogestin (RU 486) on treatment days 30, 60, 90, 120, 150, and 180; (3) same as group 2, except that the progesterone antagonist was given only on days 60, 120, and 180; (4) same as group 2, except that RU 486 was given only on days 90 and 180; and (5) 180 days of continuous estrogen-progestin daily therapy, but without any antiprogestin treatment. Daily monitoring to detect vaginal blood, as in Part I above, was discontinued at 187 days. Femoral blood was collected once weekly throughout in order to identify potential breakthrough ovulation via progesterone elevations; serum values above 1.0 ng/ml were considered indicative of ovarian luteal function and possible ovulation. Likewise, these same specimens were analyzed for estradiol levels in order to monitor ongoing endogenous estrogen biosynthesis. Two monkeys, in groups 1 and 3, respectively, were dropped from the ongoing protocol, one due to a skin rash and the other because of a thumb infection requiring topical treatment. Neither incident is believed to be related to the hormonal treatments.

Medications

To achieve ultra low dose oral contraception and to adjust the commercial medication used to the smaller (than human) body weight of these laboratory primates, an oral dose of 1.2 μg/day of ethinyl estradiol and 0.06 mg/day of norethindrone acetate was employed. This was achieved by grinding to a powder a commercially available pill ("Loestrin 1/20" in a conventional 21 day pack, Parke Davis, Morris Plains, N.J.), contained 1 mg of norethindrone acetate and 20 μg of ethinyl estradiol per tablet.

In the Part II cycle, cycle RU 486 "(Mifepristone", Roussel Uclaf, Paris) was administered intermittently as single 50 mg tablets in combination with the continuous estrogen-progestin oral contraceptive regimen, except the group 1 and group 5 animals. Previous studies had indicated that this dose of RU 486 would be sufficient to displace natural progesterone from endometrial, myometrial and cervical receptors, thereby inducing prompt (usually within 48 hours) and complete sloughing of both uterine fundal and isthmic tissue, comparable to spontaneous menstruation. See Healy D L, et al., "Fertil Steril" 1983; 40:253; Danforth D R et al., Contraception 1989; 40:199. Because the estrogen and progestin components were already combined, progestin was included even during the intervals of RU 486 administration.

In terms of comparison to human dose equivalents, the daily dose received by the monkeys, with a monkey's body weight about 6 kg and a woman's at 60 kg, was about 12 mg of ethinyl estradiol and 0.6 mg of norethindrone acetate. Thus, this ultra low dose oral contraceptive formulation presented a 40% reduction in daily estrogen-progestin exposure compared to one of the lowest dose combination oral contraceptives commercially available today in America or Europe. Even taking into account that when a continuous ultra low dose regimen was used, versus the traditional 21+7 day protocol, there would be 92 more treatment days on an annualized basis, the treatment reduced the annual rate of exogenous estrogen-progestin exposure by more than 20%.

Statistical Evaluations and Results

Differences between group results in study Part I, calculated as the means and standard errors, were compared using the F statistic, testing at P<0.05 level of significance.

Although two of the menstrual factors monitored (breakthrough bleeding rates and duration of withdrawal ("pill-free") menses did not reveal any significant differences (P>0.05), certain trends were observed, viz., (1) the breakthrough bleeding rates were noticeably lower in cycles 2 and 3; and (2) the duration of withdrawal menses in the "pill-free" interval was slightly less each month. In turn, the incidence of withdrawal amenorrhea (the third menstrual factor which was monitored) at the time of expected withdrawal menses did increase significantly (P<0.05) in treatment cycle 3 versus 1. Circulating levels of estradiol and progesterone reflected indirectly the inhibitory actions of the estrogen-progestin medication on pituitary gonadotropin secretion. Although serum estradiol rose clearly during the "pill-free" intervals adjacent to the treatment days in cycle 2, follicular maturation was curtailed by reinstitution of medication, as indicated by highest levels around 60 pg/ml without therapy and suppression to near 25 pg/ml on day 21. Since serum progesterone levels remained at or near the lower detection limits of the assay throughout, the data firmly indicate that ovulation probably was blocked reliably in all 32 monkeys.

Data derived from Part II of the study was listed by treatment group with the profiles of endometrial bleeding through six treatment cycles to 180 days. Mean (+SEM) number of days for breakthrough bleeding or menses was calculated by dividing the total number of incidents recorded (per treatment cycle in the case of group 1 or 30 days intervals for groups 2 to 5) by the number of individuals observed in the group. In the tabulation of data, menses (withdrawal or induced bleeding at expected intervals) was scored for vaginal blood detected within the "pill free" interval for group 1 or within seven days after the intermittent administration of RU 486 during continuous ultra low dose oral contraception (groups 2 to 4). Similarly, failure to observe vaginal bleeding during these times of expected menses, either withdrawal of the oral contraceptive medication or soon after giving the progesterone antagonist, was scored as withdrawal amenorrhea.

For group 1, the incidence of breakthrough bleeding changed little from the 1st to 6th treatment cycle. However, the data overall obtained in Part II compared to that in Part I showed a 2.4 fold reduction (P<0.05) in the breakthrough bleeding rates, progressively. Statistical significance (P≦0.05) was reached also in treatment cycles 3 and 6 of Part II versus treatment cycle 1 of Part I.

For groups 2 to 4 in association with the intermittent single doses of RU 486 at 30, 60, or 90 days intervals, the overall breakthrough bleeding incidence was reduced by 57% (P<0.05) when the statistical comparison was made for total combined data from groups 2 to 4 versus group 1. However, group 5 manifested a unique response to continuous ultra low dose oral contraception. The frequency of breakthrough bleeding rose moderately in the 5th and markedly in the 6th 30-day interval compared to all other study groups (P<0.05).

With regard to pill withdrawal or RU 486 induced menses, the ultra low dose oral contraceptive, administered in a traditional 21+7 day regimen, resulted in fewer (P<0.05) days of menstrual flow than in the pretreatment spontaneous menstrual cycle (1.7±0.5 days, overall versus 3.7±1.6 days, respectively); menses after RU 486 was of longer duration (3.1±0.8 day; P<0.05) than with the interrupted pill cycle alone. There were no significant differences in bleeding profiles among RU 486 treated groups (P>0.05). Lastly, those primates receiving an uninterrupted course of ultra low dose oral contraceptive medication for 180 days (group-5) demonstrated a longer duration of withdrawal menses than other treated group (4.9±3.5 days, P<0.05). However, the degree of individualism observed prevented achieving statistical significance (P>0.05) from findings in the pretreatment cycle.

The incidence of amenorrhea in Part II was noticeably reduced when RU 486 was added intermittently to the continuous oral contraceptive regimen. In fact, no monkeys failed to bleed after RU 486, although for some the presence of vaginal blood was as brief as one or two days. In contrast, when either the 21+7 day conventional regimen or continuous administration of the ultra low dose oral contraceptive alone was used, the incidence of amenorrhea ranged between 20 and 30% overall (P<0.05).

Throughout Part II, weekly serum progesterone levels remained below 1.0 ng/ml, except for one instance when a value of 1.4 ng/ml was found. Reassay of this specimen produced a concentration of 0.26 ng/ml, suggesting that the initial value may have resulted from a spurious assay, rather than indicating possible elevated ovarian follicular or luteal activity. Concurrently, overall serum estradiol concentrations during the 180 day study were 37±19, 23±7, 27±7, 22±5, 25±3 and 26±6 pg/ml for groups 1 to 5, respectively, illustrating overall significantly (P<0.05) lower estrogen levels during continuous ultra low dose oral contraceptive regimens, irrespective of RU 486.

These findings are consistent with the ultra low dose oral contraceptive employed being sufficient to block ovulation when using either a conventional regimen of 21 days of medication plus 7 "pill free" days or uninterrupted treatment for 180 days. However, the incidence of bleeding problems, either breakthrough bleeding or withdrawal amenorrhea in the "pill free" interval was increased, irrespective of whether the treatment regimen was the traditional 21+7 days scheme or was extended continuous therapy, compared to when RU 486 was given in conjunction with the estrogen/progestin therapy.

Addition of the antiprogestin RU 486 intermittently at 30, 60, or 90 day-intervals was associated with two improvements in the bleeding profiles. Reduced breakthrough bleeding in the intermenstrual intervals and reliable menstrual induction at the expected time was observed, thus eliminating withdrawal amenorrhea. Also, overall, the duration of induced menstrual flow was slightly greater after RU 486. When continuous oral contraceptive treatment was used without RU 486, the frequency of breakthrough bleeding rose measurably in the 5th and, especially, the 6th 30 day interval. Like-treated females that received single administrations of the progesterone antagonist at 30, 60, or 90 day intervals consistently experienced the lowest (57% less) breakthrough bleeding rates compared to findings when the traditional 21+7 day scheme or continuous dosing, but without the antiprogestin.

The frequency of breakthrough bleeding among women beginning oral contraceptive use is known to be higher in the initial pill cycles than subsequently. It is believed that this often reported observation may reflect both a biological effect of hormonal adjustment to the medication as well as unreliable user compliance among women not experienced with oral contraceptives. The results of the above-described experiments in this primate model are consistent with such opinions in part; viz., a progressive decline in breakthrough bleeding incidence was observed through the initial 3 to 4 months of treatment with an ultra low dose oral contraceptive administered in a conventional 21+7 day regimen. Although the observed absolute frequency of breakthrough bleeding was lower than that often reported in women, this may be due to enforcement of compliance experimentally on the monkeys and/or other differences related to dose, regimen or species. Moreover, having stabilized these primates on this cyclic treatment schedule for three cycles in Part I before segregating them into the five groups of Part II may have improved our insight into the impact of RU 486 on bleeding control problems associated with low dose oral contraceptive use. Not only was RU 486 consistently related to significantly less breakthrough bleeding, but the antiprogestin reliably induced some bleeding in all instances within 72 hours, whether administered at 30, 60 or 90 day intervals. Without intermittent RU 486 treatment, the incidence of amenorrhea at expected bleeding times was elevated with both the 21+7 conventional regimen and the 180 day continuous treatment alone (group 5). The latter data suggest that continuous oral contraceptive regimens require occasional sloughing of the endometrial to avert cumulative bleeding irregularities.

From the foregoing data, several possible explanations can be given for the improved, bleeding control during the continuous ultra low dose regimen of oral contraception plus intermittent RU 486. For example, serum estradiol levels were almost unvarying, hovering near 25 pg/ml, and absence of the secretory bursts of estradiol that characterize the "pill free" interval during transient "follicular escape" when traditional 21+7 day regimens are used RU 486 treatment may act in three ways: (1) constraint by its antimitogenic properties on endometrium, on modulating rapid endometrial proliferation; (2) negating an excessive degree of progestin over estrogen dominance (here the ratio of norethindrone acetate: ethinyl estradiol is 50:1); and (3) extended continuous oral contraceptive regimens that cause accumulation of endometrial tissue, and ultimately higher breakthrough bleeding rates, can be offset by occasional sloughing of tissue.

Overall, the findings of this primate study are consistent with the feasibility of (1) further reductions in the daily dose of estrogen-progestin oral contraceptives; (2) continuous ultra low dose oral contraceptive regimens, wherein the daily pill-taking interval is extended to 30, 60, and 90 days without interruption; and (3) a single intermittent dose of an antiprogestin in combination with continuous oral contraceptive regimens to reduce intermenstrual breakthrough bleeding rates and to insure avoidance of withdrawal amenorrhea, both of which are known to be associated with today's lower dose oral contraceptive regimens.

Thus, the present invention is useful in increasing oral contraceptive safety, user satisfaction and user compliance, without comprising contraceptive efficacy. Moreover, because contraceptive efficacy in women is not sacrificed and may, in fact, be enhanced by a continuous estrogen/progestin regimen which does not require user memory of stop-start days, as with a 21 day cycle pill package and the major patient compliant of menstrual nuances is meaningfully reduced by intermittent inclusion of an antiprogestin, ultra low dose estrogen/progestin oral contraceptives thus become increasingly desirable for sexually active women from their teenage years through menopause.

Additionally, although some women desire from their cyclic oral contraceptive medication a regular withdrawal menses every 4 weeks (13 times annually), others would prefer a less frequent menstrual flow, assuming a safe and efficacious product designed to insure menses less often, such as only 4 times per year, existed. The present invention, which employs a combination of low dose estrogen-progestin pill in a continuous regimen, in combination with an antiprogestin administered only at extended intervals, when a menses is desired or medically indicated, provides such a product.

Also, withdrawal menses in some post-menopausal women, whether using sequential or concurrent estrogen-progestin therapy is a major cause of failed user compliance. A therapeutic regimen in accordance with this invention can overcome the patient disfavor of frequency cyclical vaginal bleeding without sacrificing safety and effectiveness, by the use of continuous estrogen replacement therapy, in conjunction with a progestin with intermittent use of antiprogestin to shed accumulated endometrial tissue only a few times yearly, motivates post-menopausal patients, via less frequent menses, to remain on hormone replacement therapy with its apparent long-term advantages to cardiovascular integrity and bone maintenance.

In the case of hormone replacement therapy the major patient compliant of breakthrough bleeding is significantly reduced by intermittent inclusion of an antiprogestin due to its antimitotic activity which may supplement the inhibitory effects of progestin itself on endometrium growth and its beneficial action on the vascular bed of the endometrium. The withdrawal bleeding following antiprogestin administration may not necessarily occur because of the lack of endometrial transformation by a progestin.

Example II

Intermittent Antiprogestin During Estrogen and Estrogen Plus Progestin Replacement Therapy Primates Twenty previously ovariectomized cynomolgus monkeys (*Macaca fascicularis*) have implanted for 281 days a single estradiol-containing subcutaneous capsule. Estradiol release from this capsule results in serum estradiol concentrations of approximately 75 pg/ml. A subcutaneous progesterone capsule is implanted on day 191 and remains in place until day 281. Progesterone release from this capsule results in serum progesterone concentrations of approximately 4 ng/ml. The study takes place in the animal research facilities of the Eastern Virginia Medical School as described in Example I.

Study Design

The purpose of this study was to evaluate break-through bleeding prior to and after onapristone treatment in ovariectomized monkeys receiving estrogen and estrogen plus progesterone replacement therapy. The twenty monkeys were assigned to the following four groups: Group I receives onapristone vehicle (saline) on days 30, 60, 90, 120, 150, 180, 210, 240, 270. Group 2 receives 3 mg/kg i.m. onapristone on days 30, 60, 90, 120, 150, 180, 210, 240, 270. Group 3 is treated with 10 mg/kg i.m. onapristone on the same days. Group 4 receives 30 mg/kg i.m. onapristone on the same days. Vaginal swabs are performed daily from day 1 to 281. The primary parameter for evaluation in this study is the occurrence of vaginal bleeding.

Results

The progressing duration of estradiol treatment results in the increasing rate of breakthrough bleeding in the vehicle treated group (Group 1). Onapristone treatment in Groups 2-4 does not induce bleeding but it lowers the incidence of breakthrough bleeding. Once combined estradiol and progestin treatment has been initiated, onapristone induces vaginal bleeding.

Example III

Hormone Replacement Therapy

Primates

Twenty ovariectomized cynomolgus monkeys were implanted subcutaneously with an estradiol-containing silastic capsule (3 cm length). Estradiol release from this capsule resulted in serum estradiol concentrations of approximately 75 pg/ml.

The study was undertaken in two phases.

All monkeys have reached at least day 272. The estradiol implant will remain in place to day 301. A progesterone implant (3 cm) which resulted in serum progesterone concentrations of approximately 4 ng/ml was in place from day 185 to 210. A smaller progesterone implant (0.5 cm) will be in place from day 210 to 294. This implant is intended to produce a serum progesterone concentration of approximately 0.7 ng/ml. The two experimental groups (M=10/group) were as follows:

Group 1 Onapristone vehicle (saline) on days 180, 197, 240, and 270

Group 2 Onapristone vehicle (40 mg/kg, im) on days 180, 197, 240, and 270

In Group 1 (vehicle) 33 days of vaginal bleeding have occurred during 865 days of observation. The bleeding has occurred in three of the ten monkeys. None of the bleeding was associated with the vehicle treatments nor the removal of the larger progesterone implant.

In Group 2 (onapristone, 40 mg/kg) 20 days of vaginal bleeding have occurred out of 800 days of observation. The bleeding has occurred in seven of the ten monkeys. Twelve of the twenty days of bleeding followed the day 197 onapristone treatment; bleeding followed this treatment in four of the ten monkeys. Six of the twenty days of bleeding followed the day 240 onapristone treatment in one monkey. Therefore, of the days of bleeding, only two can be classified as unscheduled bleeding (breakthrough bleeding). These two days of unscheduled bleeding occurred on days 193 and 195 in two different monkeys.

Results and Conclusions

During the control (Group 1) monkeys exhibited 33 days of unscheduled vaginal bleeding. The onapristone treated monkeys (Group 2) exhibited only 2 days of unscheduled vaginal bleeding. The onapristone treatment of 40 mg/kg, im reduced the incidence of breakthrough bleeding which occurs with estradiol and low-dose progesterone hormone replacement therapy.

The results of this study show that:

1. Ovariectomized cynomolgus monkeys substituted with $E_2$ alone do not exhibit breakthrough bleedings (BTBs).

2. There was an increase in BTBs after an addition of low-dose progesterone. This finding suggests that the BTBs are dependent on progesterone.

3. Onapristone induced withdrawal-bleeding in ovariectomized monkeys substituted with $E_2$ and low-dose progesterone.

4. Onapristone reduced the incidence of BTBs in ovariectomized monkeys substituted with $E_2$ and low-dose progesterone (2 days of unscheduled bleeding (treatment group) versus 33 days of unscheduled bleeding (controls).

This invention, inter alia, relates to a method of avoiding BTBs in estrogen-HRT and estrogen/progestin-HRT by intermittent anti-progestin treatment. In the case of estrogen plus low-dosage HRT, low-dose progestin will be introduced to suppress the estradibl-induced mitotic activity in the endometrium (endometrial protection without inducing negative effects on the plasma lipids). Intermittent antiprogestin is used:

(1) to induce endometrial bleeding (elimination of the endometrium additionally reduces the risk of endometrial cancer), and (2) to reduce the incidence of BTBs.

A low-dose of a progestin is defined as the amount which suppresses the mitotic activity of $E_2$ in the endometrium but which does not produce secretory changes in the endometrium and has no negative effects on the plasma lipids (predominantly HDL). See Lobo, Regerio A. Am. I. Obstergynecol., 166 (6, part 2) 1997 (June, 1992).

Kit Example

A kit is provided which contains 28 unit doses conventional tablets adapted for oral ingestion, each containing 12 mcg. of the estrogen ethinyl estradiol and 0.6 mg of the progestin norethindrone acetate.

(a) In one embodiment, the tablets are arranged in a conventional circular or elongated "racetrack" oval configuration, with indicia corresponding to the days of the week, so that compliance with the daily intake regimen can readily be confirmed by the patient.

For an example of such products, see Berlex Laboratories "Levien-28". The tablet arranged to be taken on the 21st or later day contains, in addition to the ethinyl estradiol and norethindrone acetate, 500 mg. of the anti-progestin RU 486 ("Mifepristone", Roussel Uclaf).

(b) In another embodiment, 20 or more e.g., 20, 23, 24, 30, 60, 90 or 120, tablets containing only the estrogen and progestin or only the estrogen are packaged loosely in a container, e.g., a bottle with flat faces or a flat metal box with a snap open top such as is conventionally used to hold aspirin tablets, or like container. Packaged separately, e.g., in an accessible cavity in the bottle cap or in a bubble pack adhesively affixed to one face of the bottle or the metal box, is a tablet containing the anti-progestin alone or in admixture with the estrogen and progestin. On the package for this tablet is provided space for the physician (or patient) to write the day and the month when the tablet instead of (when the tablet contains both the anti-progestin and the estrogen and progestin) or in addition to the other tablets (when the tablet contains only the anti-progestin) should be taken to induce menses. The kit contains the number of tablets required to provide continuous estrogen/progestin therapy for one menstrual cycle of 28, 30, 60, 90 or 120 days duration.

(c) In another version of the above-described kits otherwise corresponding to the first embodiment (s), amounts of the estrogen and progestin vary, i.e., in the first 7 tablets, the amounts thereof are 35 mcg. and 1.5 mg. per tablet, respectively,; in the next 7, they are 30 mcg. and 0.8 mg. per tablet, respectively; in the next 7, they are 20 mg. and 0.6 mg. per tablet, respectively; and in the last 7, they are 5 mcg. and 0.4 mg. per tablet, respectively.

(d) In variations of each of the kits described hereinabove, the norethindrone acetate in the tablets is replaced by 25 mcg. of gestodene.

(e) In other variations of each of the kits described hereinabove, the estrogen therein is replaced by 20 mcg. of mestranol.

(f) In other variations of each of the kits described above, the antiprogestin therein is replaced by 500 mg. of onapristone.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of hormone replacement therapy, comprising administering to a woman in need thereof an effective amount of estrogen in combination with an effective amount of a progestin, and an amount of antiprogestin effective to ameliorate uterine bleeding problems associated with hormone replacement therapy.

2. A method of claim 1, wherein the antiprogestin is administered periodically.

3. A method of claim 1, wherein the antiprogestin is administered continuously.

4. A method of hormone replacement therapy comprising administering to a woman in need thereof an effective amount of estrogen, with progestin administration, and an amount of antiprogestin effective to inhibit breakthrough bleeding.

5. A method of claim 4 wherein the antiprogestin is administered periodically.

6. A method of claim 4, wherein the antiprogestin is administered continuously.

7. A method of claim 5, wherein the estrogen is administered continuously.

8. A method of claim 6, wherein the estrogen is administered continuously.

9. A method of hormone replacement therapy comprising administering to a woman in need thereof an effective amount of estrogen, with progestin administration, and an amount of antiprogestin equivalent to an oral dose of about 1.0 to about 10 mg/kg of weight of the woman.

10. A method of claim 9, wherein the antiprogestin is administered periodically.

11. A method of claim 9, wherein the antiprogestin is administered continuously.

12. A method of claim 10, wherein the estrogen is administered continuously.

13. A method of claim 11, wherein the estrogen is administered continuously.

14. A method of claim 9, wherein the dose is 50-500 mg.

15. A method of avoiding the bleeding problems associated with administering to a female mammal dosage amounts of an estrogen low enough to create incidents of breakthrough bleeding and withdrawal amenorrhea during hormone replacement therapy, which comprises (a) administering the estrogen daily without interruption and (b) administering progestin and (c) periodically, at intervals of at least about a month, administering to the female an amount of an antiprogestin effective to reduce or eliminate breakthrough bleeding and, optionally, to induce sloughing of accumulated endometrial tissue and thereby induce menses.

16. A method of claim 15, wherein the estrogen and the daily dose thereof is ethinyl estradiol or an ester thereof in the amount of 5-15 mcg/day, mestranol in the amount of 20-25 mcg/day or conjugated estrogens in the amount of 5-15 mcg/day.

17. A method of claim 15, wherein the amounts of the estrogen and the progestin which are administered are effective to suppress endometrial proliferation.

18. A method of claim 15, wherein the administration of the progestin is continued uninterrupted throughout the cycle.

19. A method of claim 15, wherein the administration of progestin is interrupted proximate the day of antiprogestin administration.

20. A method of claim 15, wherein the antiprogestin is administered about monthly.

21. A method of claim 15, wherein the antiprogestin is administered orally.

22. A method of claim 15, wherein the antiprogestin is onapristone or mifepristone.

23. The method of claim 15, wherein the progestin is gestodene or norethindrone acetate.

24. The method of claim 15, wherein the estrogen, the progestin and the antiprogestin are administered orally; wherein the administration of the progestin and the estrogen is continued uninterrupted throughout the cycle and wherein the estrogen and the daily dose thereof is ethinyl estradiol or estradiol or an ester thereof in the amount of 5-15 mcg/day, mestranol in the amount of 20-25 mcg/day or conjugated estrogens in the amount of 5-15 mcg/day.

25. The method of claim 15, wherein the female is a para- or postmenopausal woman.

26. The method of claim 25, wherein the estrogen is administered in combination with a progestin.

27. The method of claim 26, wherein the administration of the progestin is continued uninterrupted during the period of antiprogestin administration.

28. The method of claim 26, wherein the administration of the progestin is interrupted proximate the period of antiprogestin administration.

29. The method of claim 25, wherein the antiprogestin is onapristone or mifepristone.

30. The method of claim 25, wherein the estrogen and the daily dose thereof is ethinyl estradiol or estradiol or an ester thereof in the amount of 5-15 mcg/day, mestranol in the amount of 20-25 mcg/day or conjugated estrogens in the amount of 5-15 mcg/day.

31. The method of claim 26, wherein the antiprogestin is onapristone or mifepristone; and wherein the progestin is gestodene or norethindrone acetate.

32. The method of claim 26, wherein the estrogen, progestin and antiprogestin are administered orally; wherein the antiprogestin is administered at longer than one month intervals; wherein the administration of the progestin is continued uninterrupted during the period of antiprogestin administration; and wherein the estrogen and the daily dose thereof is ethinyl estradiol or estradiol or an ester thereof in the amount of 5-15 mcg/day, mestranol in the amount of 20-25 mcg/day or conjugated estrogens in the amount of 5-15 mcg/day.

33. The method of claim 15, wherein the estrogen is ethinyl estradiol.

34. The method of claim 25, wherein the antiprogestin is administered at longer than monthly intervals.

35. The method of claim 25, wherein the administration of the progestin and estrogen is continued uninterrupted throughout the cycle, including during menses.

36. The method of claim 35, wherein the administration of the progestin is interrupted proximate the day of the antiprogestin administration.

37. The method of claim 25, wherein the antiprogestin is administered orally.

38. The method of claim 25, wherein the antiprogestin is mifepristone.

39. The method of claim 25, wherein the estrogen is ethinyl estradiol or estradiol.

40. The method of claim 25, wherein the progestin is norethindrone acetate.

* * * * *